(12) United States Patent
Zhou

(10) Patent No.: US 10,098,661 B2
(45) Date of Patent: Oct. 16, 2018

(54) TROCAR COMPRISING SILENCER

(71) Applicant: Guangzhou T.K Medical Instrument Co., Ltd., Guangzhou (CN)

(72) Inventor: Xing Zhou, Guangzhou (CN)

(73) Assignee: GUANGZHOU T. K MEDICAL INSTRUMENT CO., LTD., Guangzhou (CN)

( * ) Notice: Subject to any disclaimer, the term of this patent is extended or adjusted under 35 U.S.C. 154(b) by 5 days.

(21) Appl. No.: 15/588,459

(22) Filed: May 5, 2017

(65) Prior Publication Data

US 2017/0238963 A1    Aug. 24, 2017

Related U.S. Application Data

(63) Continuation of application No. PCT/CN2015/093713, filed on Nov. 3, 2015.

(30) Foreign Application Priority Data

Nov. 8, 2014   (CN) .......................... 2014 1 0631580

(51) Int. Cl.
*A61B 17/34*   (2006.01)
*A61B 17/00*   (2006.01)

(52) U.S. Cl.
CPC ...... *A61B 17/3462* (2013.01); *A61B 2017/00862* (2013.01); *A61B 2017/3464* (2013.01)

(58) Field of Classification Search
CPC ............ A61B 17/3462; A61B 17/3498; A61B 17/3423; A61B 17/3474; A61B 17/3421;
(Continued)

(56) References Cited

U.S. PATENT DOCUMENTS 5,342,315 A * 8/1994 Rowe ................. A61B 17/3462
604/167.06
5,380,288 A   1/1995 Hart
(Continued)

FOREIGN PATENT DOCUMENTS

WO   WO 95/15189 A1   6/1995

OTHER PUBLICATIONS

Guangzhou_Notice-to-File-an-Amendment-KR1020177015556 Jun. 9, 2017, 4 pgs.

(Continued)

*Primary Examiner* — Pedro Philogene
(74) *Attorney, Agent, or Firm* — Morgan, Lewis & Bockius LLP

(57) ABSTRACT

Disclosed is a trocar comprising a silencer. An end sealing assembly of a sheath of the trocar of the present application comprises an upper cover, a radial sealing assembly, a silencer and a lower cover; the silencer being an elastic body having one end installed on the radial sealing assembly and the other end installed on the lower cover; and the radial sealing assembly installed between the upper cover and the lower cover, Since the silencer holds up the radial sealing assembly, a gap between the upper cover and the radial sealing assembly is reduced, thereby avoiding an impact sound produced when a surgical instrument is withdrawn outwards, When the surgical instrument is advanced inwards, the impact sound produced when the surgical instrument is advanced inwards is avoided due to a buffer effect of the silencer.

5 Claims, 11 Drawing Sheets

(58) Field of Classification Search
CPC .... A61B 17/06061; A61B 2017/00862; A61B 2017/3464; A61B 2017/00907; A61B 2017/00955; A61B 2017/3456; A61B 2017/320044; A61B 2017/00477; A61B 2017/349; A61B 2017/3492; A61M 39/0606; A61M 39/6693; A61M 2039/0629; A61M 2039/0633; A61M 2039/0646; A61M 2039/0686
USPC ....... 600/203, 208, 227; 604/167.03, 167.06, 604/167.01, 164.01
See application file for complete search history.

(56) References Cited

U.S. PATENT DOCUMENTS

| | | | |
|---|---|---|---|
| 5,634,908 A | 6/1997 | Loomas | |
| 6,093,176 A | 7/2000 | Dennis | |
| 8,449,460 B2* | 5/2013 | Duke | A61B 17/3462 600/208 |
| 2005/0070947 A1* | 3/2005 | Franer | A61B 17/3462 606/185 |
| 2010/0274193 A1* | 10/2010 | Patton | A61B 17/3462 604/167.01 |
| 2011/0087170 A1* | 4/2011 | Insignares | A61B 17/3462 604/167.03 |

OTHER PUBLICATIONS

Guangzhou T.K. Medical Instrument Co., Communication Pursuant to Rules 161(2) and 162, EP15857795.7, Jun. 23, 2017, 3 pgs.
Guangzhou T.K. Medical Instrument Co., Extended European Search Report, EP15857795.7, dated May 22, 2018, 7 pgs.

* cited by examiner

TROCAR COMPRISING SILENCER

PRIORITY CLAIM AND RELATED APPLICATIONS

This application is a continuation application of PCT Patent Application No. PCT/CN2015/093713, entitled "TROCAR COMPRISING SILENCER" filed on Nov. 3, 2015, which claims priority to Chinese Patent Application No. 201410631580.4, entitled "TROCAR COMPRISING SILENCER ION" filed on Nov. 8, 2014, both of which are incorporated by reference in their entirety.

TECHNICAL FIELD

The present application relates to a laparoscopic surgical instrument, in particular to a trocar used in a laparoscopic surgery.

BACKGROUND

A laparoscopic surgery is applied more and more widely. In order to avoid iatrogenic infection, the consumption of a disposable trocar used in the laparoscopic surgery is increasingly greater. The trend of simplifying the structure, reducing the cost and improving the performance on the basis of ensuring the using performance has already become an improvement direction of the trocar.

In order to facilitate the surgery, it is required that the trocar can both use a 5 mm surgical instrument, and a 10 mm or 12 mm surgical instrument. Therefore, a diameter of an instrument through hole of a radial sealing ring of the trocar is generally smaller than 4 mm. When a surgical instrument with a relatively large diameter such as 10mm or 12 mm passes through the 4 mm surgical instrument through hole of the radial sealing ring, the radial sealing ring generates a relatively large surrounding force, when the surgical instrument moves back and forth, an upper pressing plate of a radial sealing ring assembly may hit against an upper cover, or a lower pressing plate of the radial sealing ring assembly may hit against a lower cover to produce an impact sound, thereby forming noise interfering a doctor. Due to the defects of the impact sound produced when the surgical instrument moves back and forth, the trocar in the prior art needs to be improved.

SUMMARY

Disclosed is a trocar comprising a silencer. The trocar 100 consists of a trocar rod 101 and a sheath 102. An end sealing assembly 1 of the sheath 102 of the trocar comprises an upper cover 11, a radial sealing assembly 12, a silencer 13 and a lower cover 14; the silencer 13 is an elastic body capable of having elastic deformation, one end of the silencer 13 is installed on the radial sealing assembly 12, and the other end of the silencer 13 is installed on the lower cover 14; and the radial sealing assembly 12 is installed between the upper cover 11 and the lower cover 14.

Further, the silencer 13 is an elastic body of a thin-wall tubular structure manufactured from a medical-use elastic material.

The elastic body of the thin-wall tubular structure of the silencer 13 comprises at least two elastic supporting legs 13-1.

In addition, the silencer 13 is an elastic body of a spring structure manufactured from a medical-use elastic material.

One end of the silencer 13 of the elastic body of the spring structure is installed in an installation hole 12-0 of the radial sealing assembly 12, and the other end is installed in an installation hole 14-0 of the lower cover 14.

The core of a technical solution of the present application lies in that:

the silencer 13 is an elastic body capable of having elastic deformation and holds up the radial sealing assembly 12, so that an upper pressing plate 12-1 of the radial sealing assembly 12 contacts the upper cover 11 of the end sealing assembly 1, or a gap between the upper cover 11 and the upper pressing plate 12-1 of the radial sealing assembly 12 is very small and is generally smaller than 0.5 mm, and in this way, when a surgical instrument 103 is withdrawn outwards, the violent impact between the upper pressing plate 12-1 and the upper cover 11 can be avoided, thereby avoiding the impact sound. When the surgical instrument 103 is advanced inwards, due to a buffer effect of the silencer 13 formed by the elastic body, the violent impact between a lower pressing plate 12-5 of the radial sealing assembly 12 and the lower cover 14 of the end sealing assembly 1 is avoided, and the impact sound is avoided, thereby avoiding the impact sound produced when the surgical instrument 103 moves back and forth, and realizing a silencing purpose.

Disclosed is the trocar comprising the silencer. The end sealing assembly 1 of the sheath 102 of the trocar of the present application comprises the upper cover 11, the radial sealing assembly 12, the silencer 13 and the lower cover 14; the silencer 13 is an elastic body capable of having elastic deformation, one end of the silencer 13 is installed on the radial sealing assembly 12, and the other end of the silencer 13 is installed on the lower cover 14; and the radial sealing assembly 12 is installed between the upper cover 11 and the lower cover 14. Since the silencer 13 holds up the radial sealing assembly 12, a gap between the upper cover 11 and the upper pressing plate 12-1 of the radial sealing assembly is reduced, thereby avoiding the impact sound produced when the surgical instrument 103 is withdrawn outwards. Meanwhile, when the surgical instrument 103 is advanced inwards, due to the buffer effect of the silencer 13, the impact sound produced when the surgical instrument is advanced inwards is avoided. In this way, when the surgical instrument 103 moves back and forth in the trocar, no impact sound is produced, thereby realizing a silencing purpose.

BRIEF DESCRIPTION OF THE DRAWINGS

FIG. 1-1 is a structural schematic diagram of an end sealing assembly of a trocar comprising a silencer of FIG. 1.

FIG. 1-2 is an exploded view of FIG. 1-1.

FIG. 1-3 is a structural schematic diagram of a silencer of a trocar comprising a silencer of FIG. 1.

FIG. 1-4 is a bottom view of FIG. 1-3.

FIG. 1-5 is a bottom view of FIG. 1-3.

FIG. 1-6 is an A-A sectional view of FIG. 1-5.

FIG. 1-7 is a working principle diagram of a trocar comprising a silencer of the present application.

FIG. 2 is a structural schematic diagram of a trocar with a silencer and a radial funnel-shaped sealing ring integrally manufactured.

FIG. 2-1 is a structural schematic diagram of an end sealing assembly of a trocar comprising a silencer of FIG. 2.

FIG. 2-2 is an exploded view of FIG. 2-1.

FIG. 2-3 is a structural schematic diagram of a silencer and a radial funnel-shaped sealing ring integrally manufactured.

FIG. 2-4 is a bottom view of FIG. 2-3.

FIG. 2-5 is a bottom view of FIG. 2-3.

FIG. 2-6 is a B-B sectional view of FIG. 2-5.

FIG. 3 is a structural schematic diagram of a trocar comprising a silencer of a spring structure.

FIG. 3-1 is a structural schematic diagram of an end sealing assembly of a trocar comprising a silencer of FIG. 3.

FIG. 3-2 is an exploded view of FIG. 3-1.

FIG. 4 is a structural schematic diagram of a trocar comprising a silencer of a spiral spring structure.

FIG. 4-1 is a structural schematic diagram of an end sealing assembly of a trocar comprising a silencer of FIG. 4.

FIG. 4-2 is an exploded view of FIG. 4-1.

In the above drawings:

Figure 1:
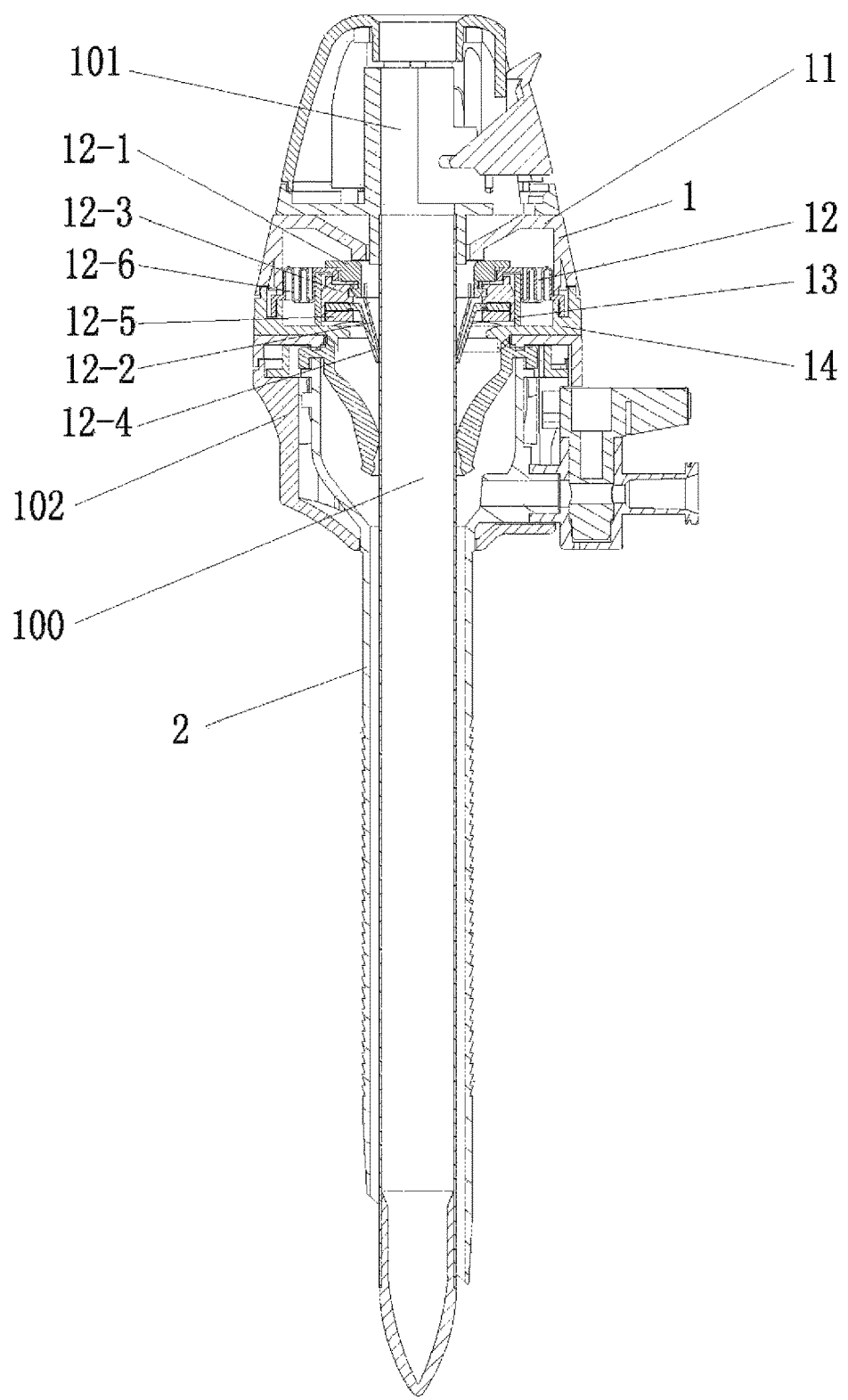
FIG. 1 is a structural schematic diagram of a trocar comprising a silencer of the present application.
Figure 1:
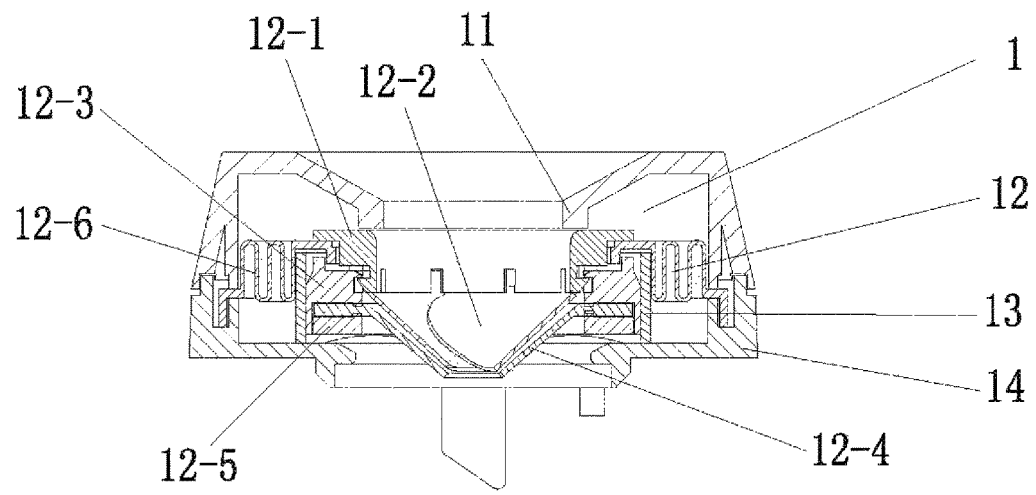
Figures 1, 2:
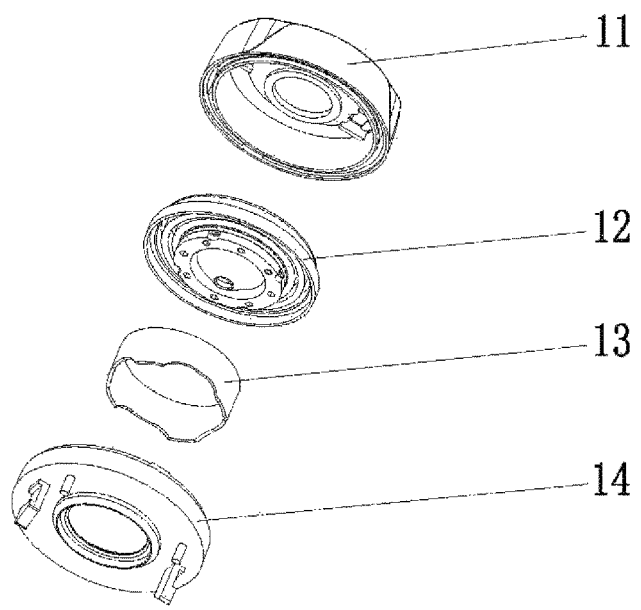
Figures 1, 2, 3:
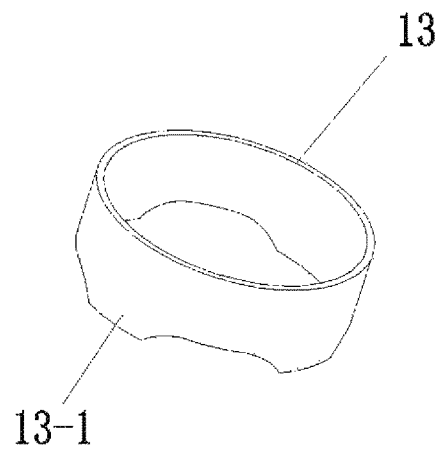
Figures 1, 2, 3, 4:
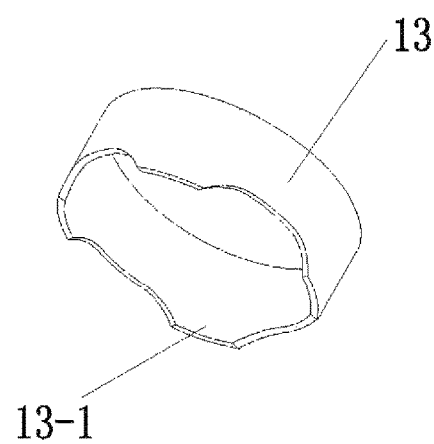
Figures 1, 2, 3, 4, 5:
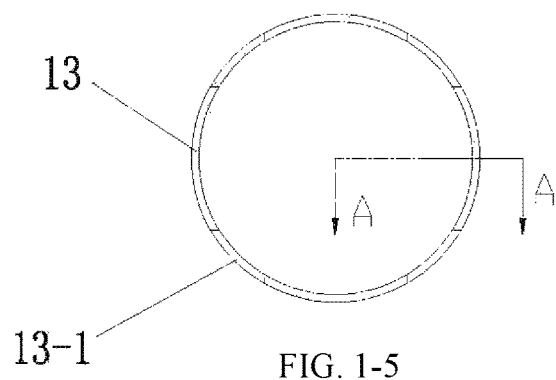
Figures 1, 2, 3, 4, 5, 6:
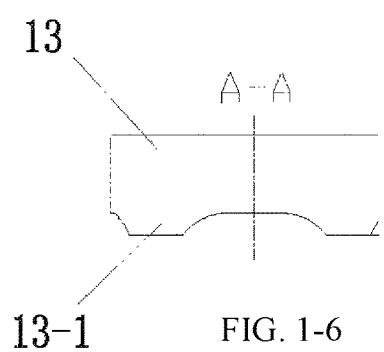
Figures 1, 2, 3, 4, 5, 6, 7:
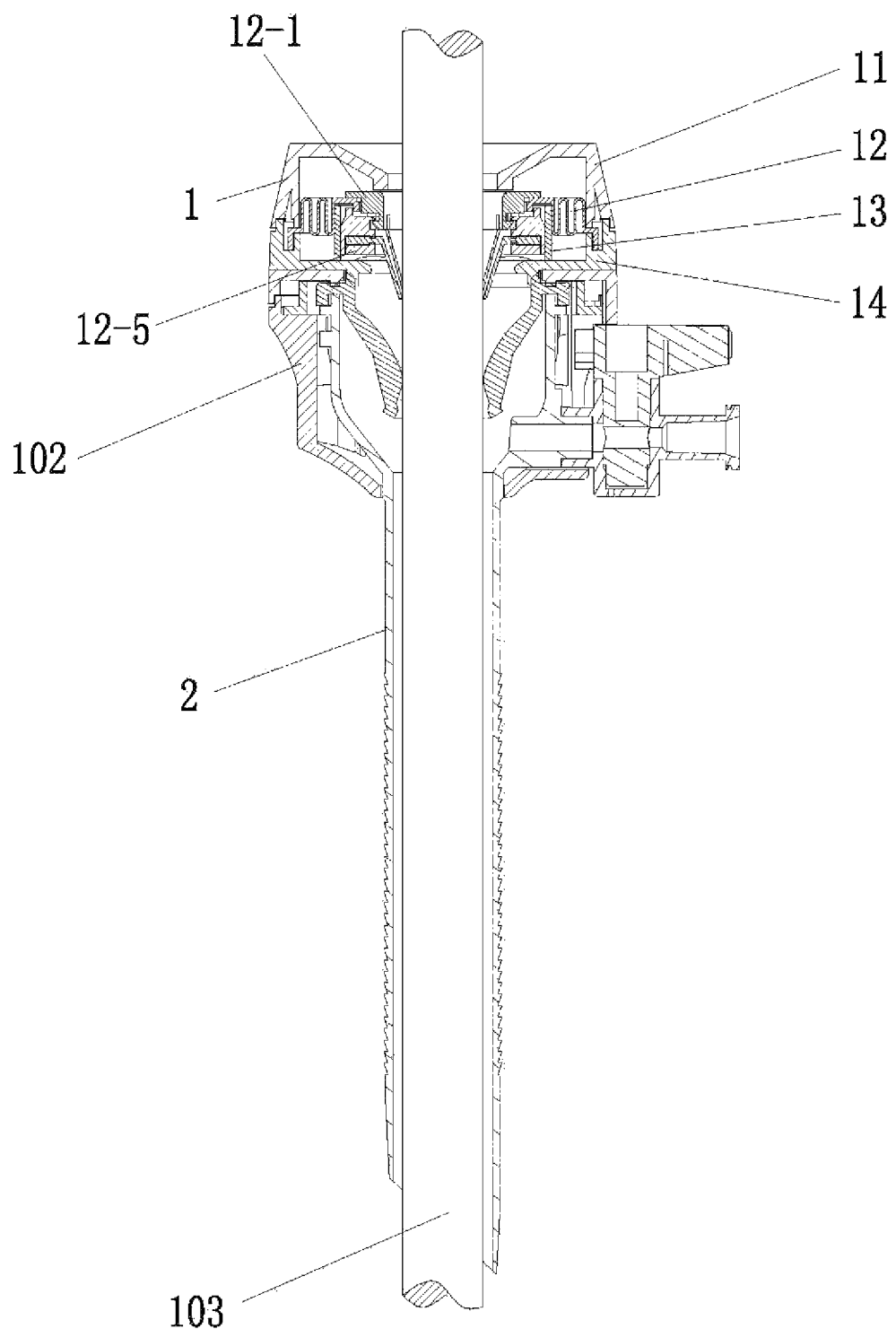
Figure 2:
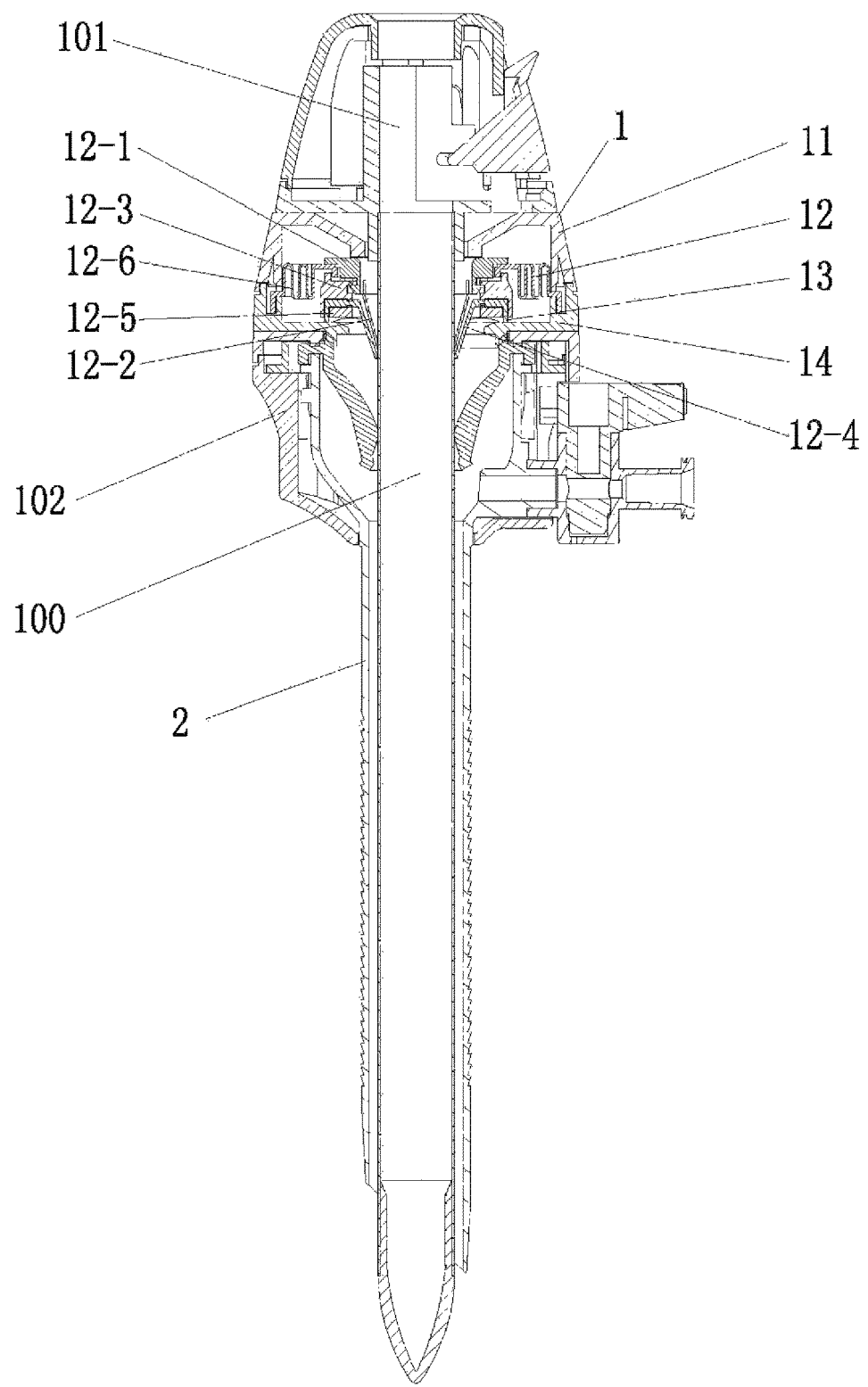
Figures 1, 2:
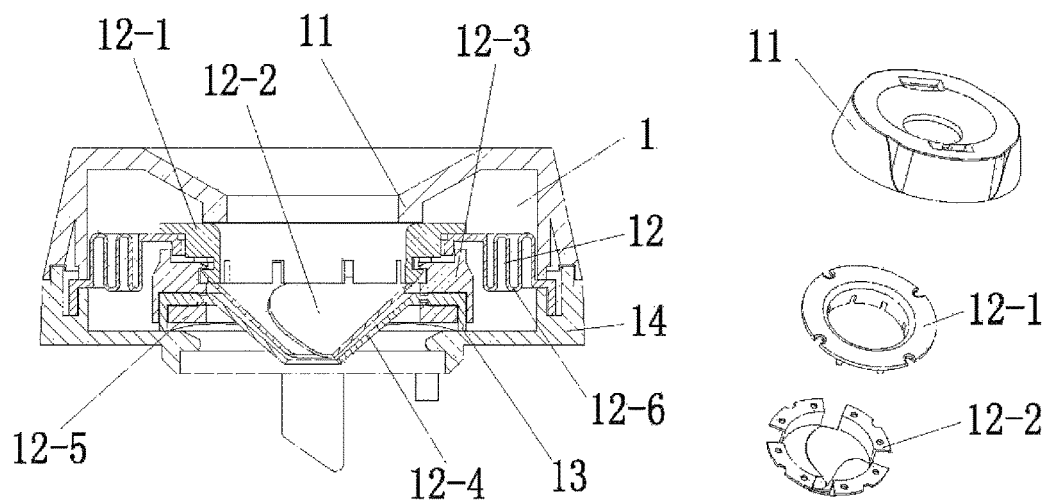
Figure 2:
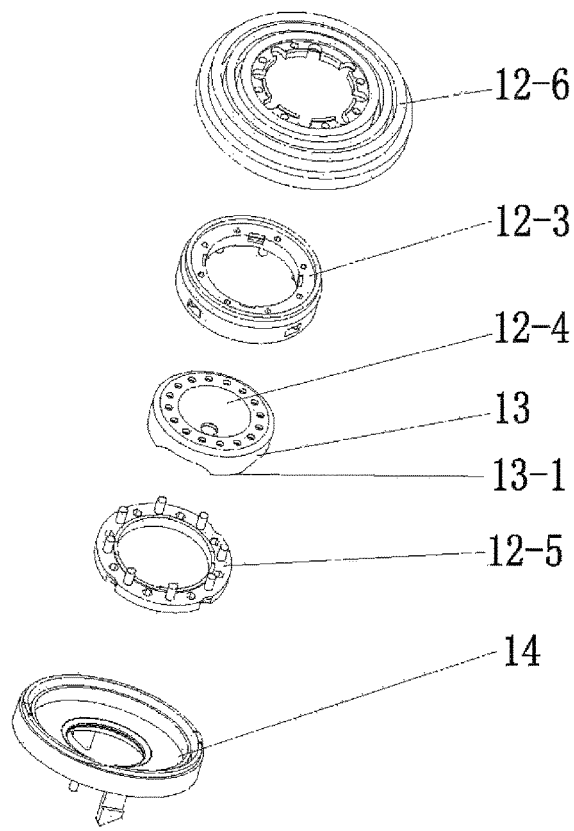
Figures 2, 3:
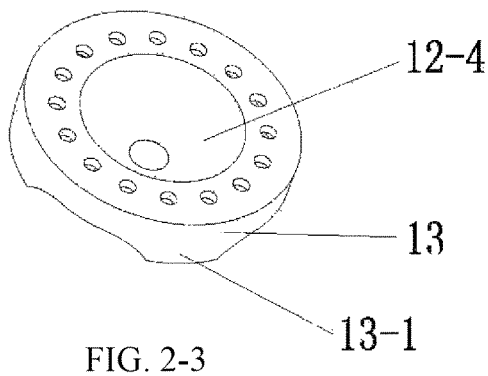
Figures 2, 3, 4:
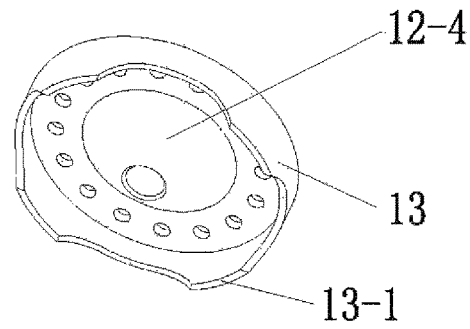
Figures 2, 3, 4, 5:
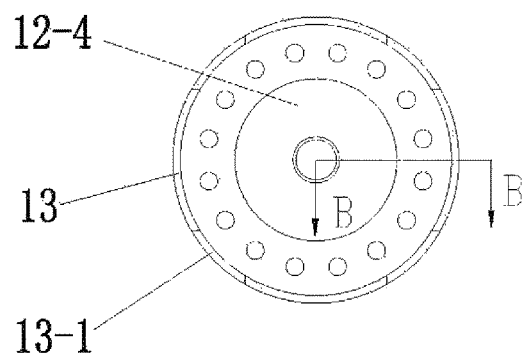
Figures 2, 3, 4, 5, 6:
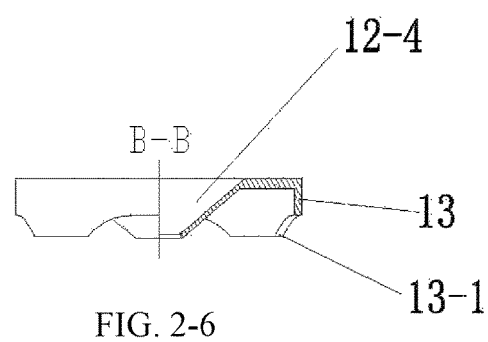
Figure 3:
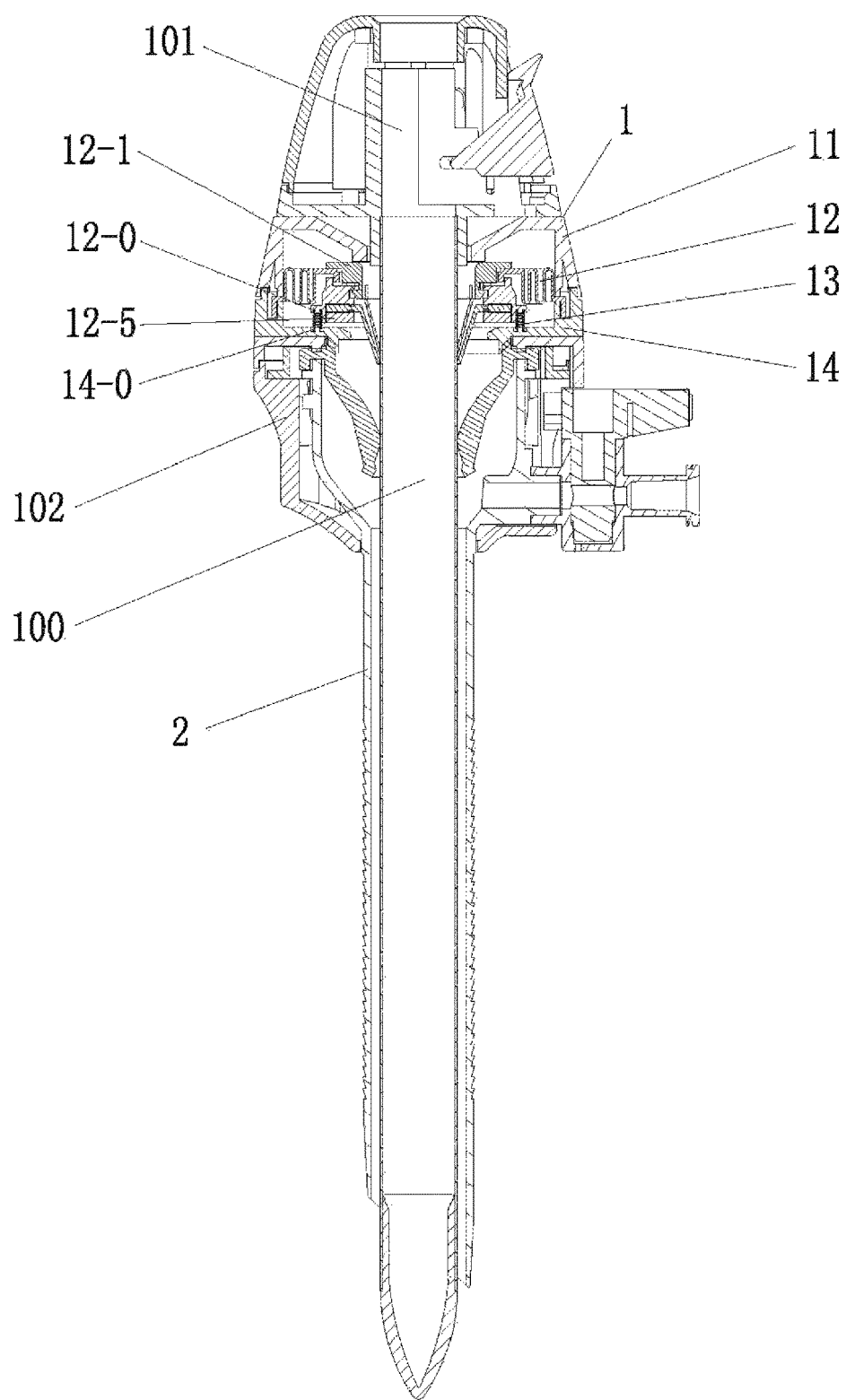
Figures 1, 3:
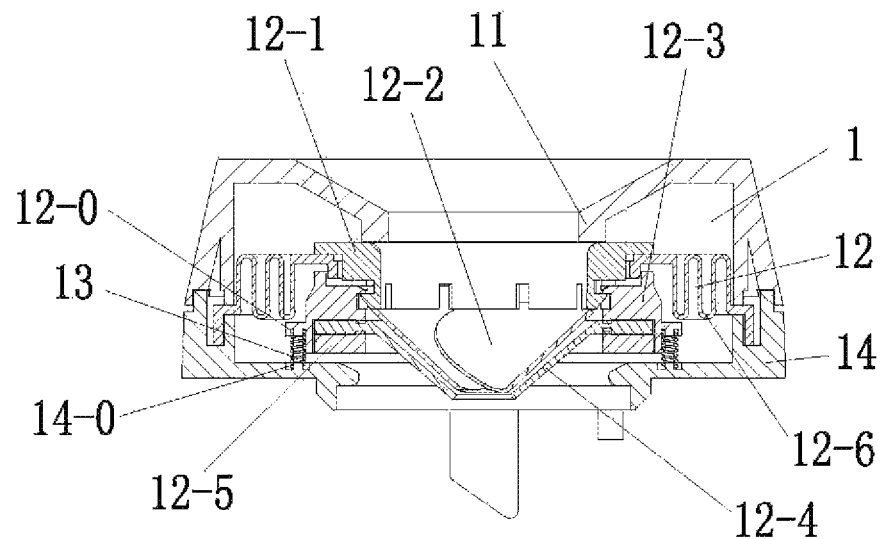
Figures 2, 3:
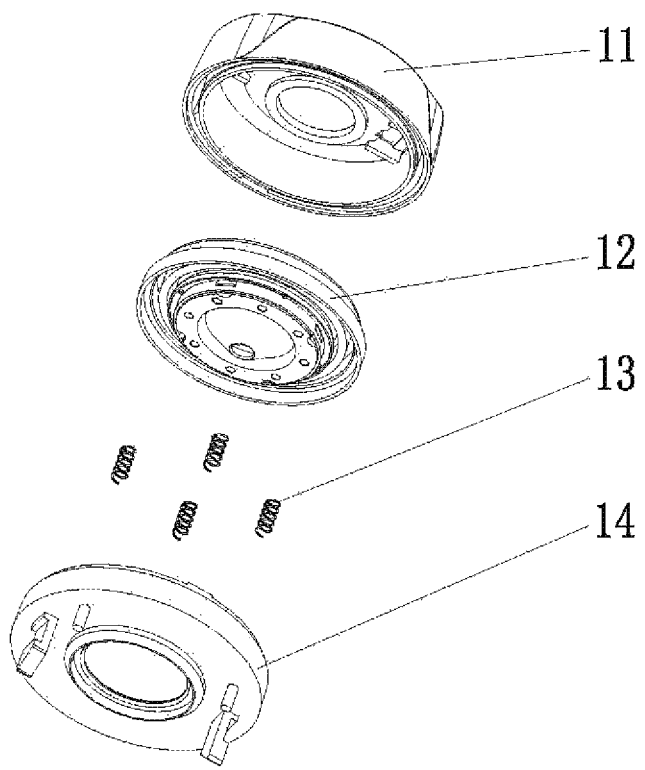
Figure 4:
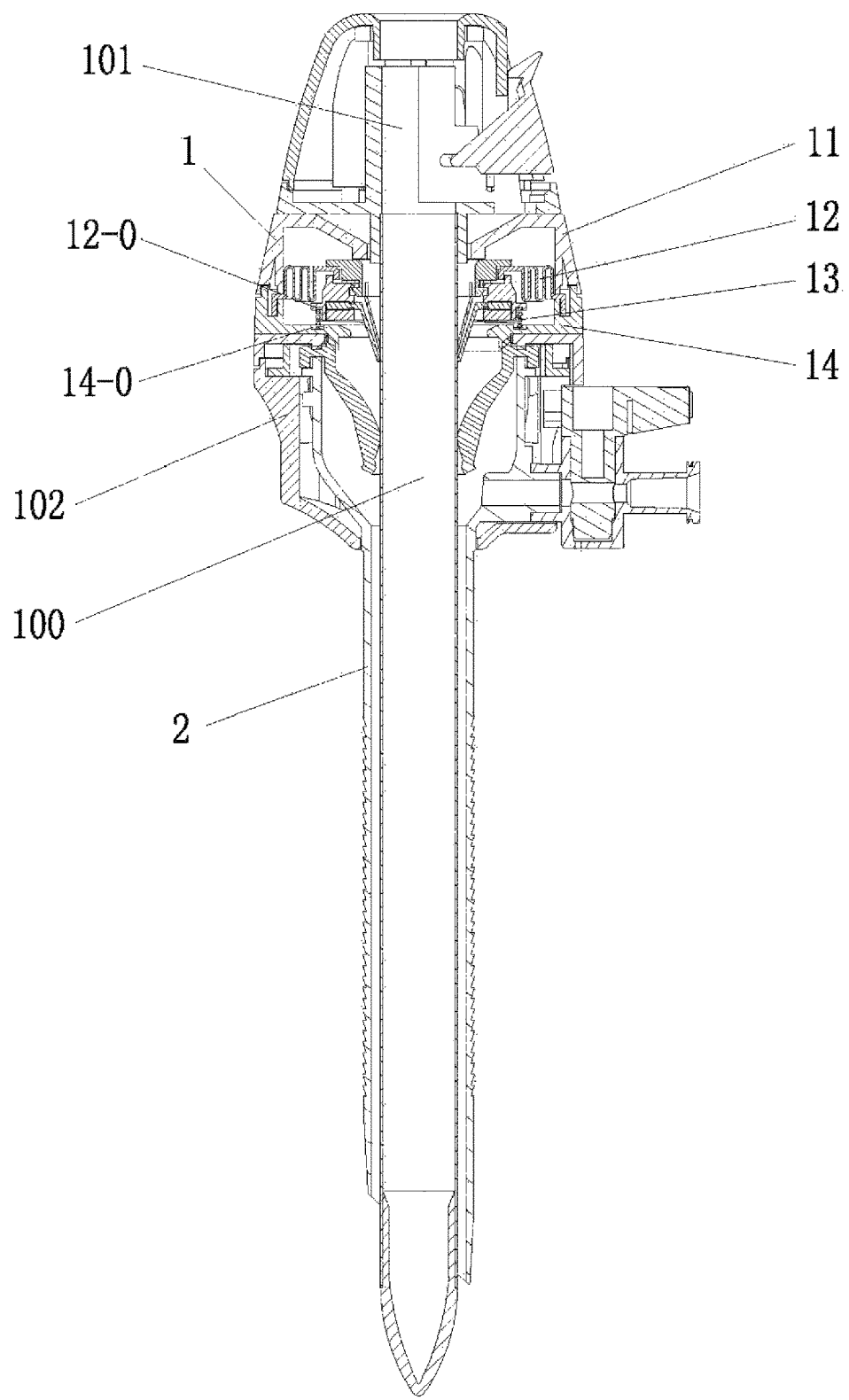
Figures 1, 4:
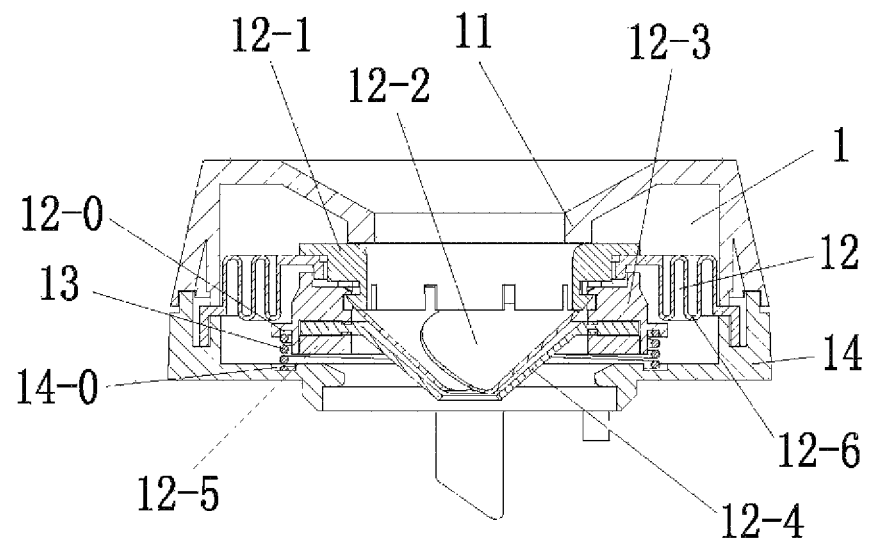
Figures 2, 4:
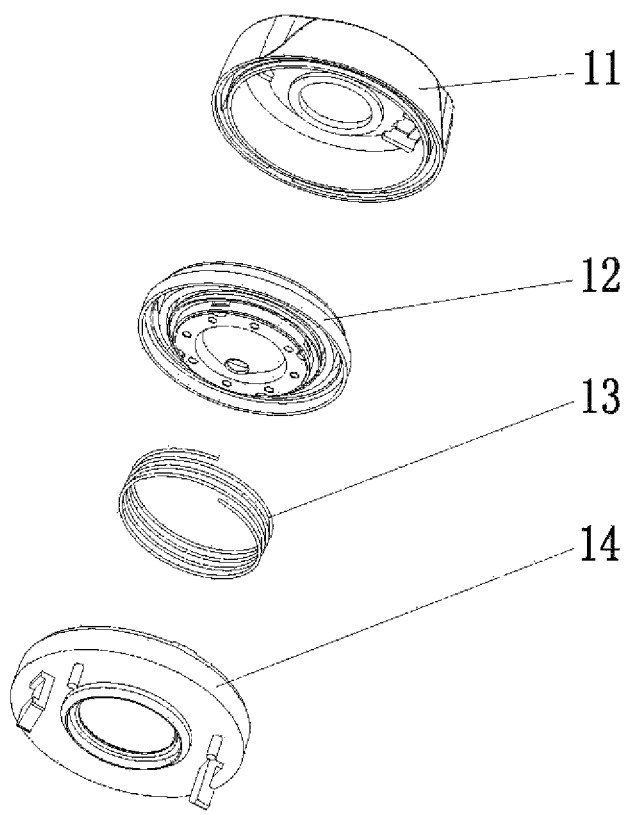

100 is a trocar comprising a silencer of the present application, 101 is a trocar rod of the trocar of the present application, 102 is a sheath of the trocar of the present application, and 103 is a surgical instrument. 1 is an end sealing assembly on the sheath of the trocar comprising the silencer of the present application, and 2 is a sleeve on the sheath of the trocar comprising the silencer of the present application.

11 is an upper cover on the end sealing assembly, 12 is a radial sealing assembly on the end sealing assembly, 13 is a silencer on the end sealing assembly, and 14 is a lower cover on the end sealing assembly.

12-0 is an installation hole of the silencer on the radial sealing assembly, 12-1 is an upper pressing plate on the radial sealing assembly, 12-2 is a sealing ring protection sheet of the radial sealing assembly, 12-3 is a positioning plate of the radial sealing assembly, 12-4 is a radial funnel-shaped sealing ring of the radial sealing assembly, 12-5 is a lower pressing plate of the radial sealing assembly, and 12-6 is a corrugated sealing ring.

13-1 is an elastic supporting leg of the silencer.

14-0 is an installation hole of the silencer on the lower cover of the end sealing assembly.

DESCRIPTION OF EMBODIMENTS

Embodiment 1: A Trocar Comprising a Silencer of a Thin-Wall Tubular Structure of the Present Application The trocar 100 comprising the silencer of the thin-wall tubular structure of the present application consists of a trocar rod 101 and a sheath 102, wherein the sheath 102 comprises an end sealing assembly 1 and a sleeve 2, and the end sealing assembly 1 is detachably installed at the upper end of the sleeve 2. The end sealing assembly 1 comprises an upper cover 11, a radial sealing assembly 12, a silencer 13 and a lower cover 14. The silencer 13 is an elastic body capable of having elastic deformation, one end of the silencer 13 is installed on the radial sealing assembly 12, and the other end of the silencer 13 is installed on the lower cover 14; and the radial sealing assembly 12 is installed between the upper cover 11 and the lower cover 14.

The radial sealing assembly 12 comprises an upper pressing plate 12-1, a sealing ring protection sheet 12-2, a positioning plate 12-3, a radial funnel-shaped sealing ring 12-4, a lower pressing plate 12-5 and a corrugated sealing ring 12-6. The radial funnel-shaped sealing ring 12-4 is installed between the positioning plate 12-3 and the lower pressing plate 12-5, and the positioning plate 12-3 and the lower pressing plate 12-5 are fixedly connected with each other. The sealing ring protection sheet 12-2 is installed between the positioning plate 12-3 and the upper pressing plate 12-1; the corrugated sealing ring 12-6 is installed between the positioning plate 12-3 and the upper pressing plate 12-1; and the positioning plate 12-3 and the upper pressing plate 12-1 are fixedly connected with each other.

The silencer 13 is an elastic body of a thin-wall tubular structure manufactured from a medical-use elastic material. In the present embodiment, the elastic body of the thin-wall tubular structure of the silencer 13 comprises four elastic supporting legs 13-1 which are manufactured from elastic medical silica gel. During installation, the upper end of the silencer 13 sleeves the positioning plate 13-3 of the radial sealing assembly 12, and the four elastic supporting legs 13-1 at the lower end of the silencer 13 are arranged on the lower cover 14 of the end sealing assembly 1. Then the upper cover 11 and the lower cover 14 are fit together, so that the radial sealing assembly 12 and the silencer 13 are installed between the upper cover 11 and the lower cover 14.

The silencer 13 holds up the radial sealing assembly 12, so that the upper pressing plate 12-1 of the radial sealing assembly 12 contacts the upper cover 11 of the end sealing assembly 1, or a gap between the upper cover 11 and the upper pressing plate 12-1 of the radial sealing assembly 12 is very small and is generally smaller than 0.5 mm, thereby avoiding the impact sound produced when the surgical instrument 103 is withdrawn outwards. Meanwhile, when the surgical instrument 103 is advanced inwards, due to the buffer effect of the silencer 13, the impact sound produced between the lower pressing plate 12-5 and the lower cover 14 when the surgical instrument is advanced inwards is avoided. In this way, when the surgical instrument 103 moves back and forth in the sheath 102 of the trocar, no impact sound is produced, thereby realizing a silencing purpose.

Embodiment 2: A Trocar with a Silencer and a Radial Funnel-Shaped Sealing Ring Integrally Manufactured of the Present Application The present embodiment differs from embodiment 1 in that the silencer 13 and the radial funnel-shaped sealing ring 12-4 of the radial sealing assembly 12 are manufactured into an integral structure by adopting an integrated manufacturing process, thereby not only reducing components, but also facilitating the installation. At the moment, the upper end of the silencer 13 is connected onto the radial sealing assembly 12, and the lower end of the silencer 13 is arranged on the lower cover 14 of the end sealing assembly 1 as that in embodiment 1.

The radial sealing assembly 12 comprises an upper pressing plate 12-1, a sealing ring protection sheet 12-2, a positioning plate 12-3, a radial funnel-shaped sealing ring 12-4, a lower pressing plate 12-5 and a corrugated sealing ring 12-6. The radial funnel-shaped sealing ring 12-4 is installed between the positioning plate 12-3 and the lower pressing plate 12-5, and the positioning plate 12-3 and the lower pressing plate 12-5 are fixedly connected with each other. The sealing ring protection sheet 12-2 is installed between the positioning plate 12-3 and the upper pressing plate 12-1; the corrugated sealing ring 12-6 is installed between the positioning plate 12-3 and the upper pressing plate 12-1; and the positioning plate 12-3 and the upper pressing plate 12-1 are fixedly connected with each other.

The silencer 13 is an elastic body of a thin-wall tubular structure manufactured from a medical-use elastic material. In the present embodiment, the elastic body of the thin-wall tubular structure of the silencer 13 and the radial funnel-shaped sealing ring 12-4 are collectively integrally manufactured from elastic medical silica gel. During installation, the upper end of the silencer 13 is fixed on the radial sealing assembly 12, and the four elastic supporting legs 13-1 at the lower end of the silencer 13 are arranged on the lower cover 14 of the end sealing assembly. Then the upper cover 11 and the lower cover 14 are fit together, so that the radial sealing assembly 12 and the silencer 13 are installed between the upper cover 11 and the lower cover 14.

Since the silencer 13 holds up the radial sealing assembly 12, a gap between the upper cover 11 and the upper pressing plate 12-1 of the radial sealing assembly is very small. When the surgical instrument moves in a reciprocating manner, the impact sound produced between the upper pressing plate 12-1 and the upper cover 11 and between the lower pressing plate 12-5 and the lower cover 14 is avoided, thereby realizing a silencing purpose.

Embodiment 3: A Trocar Comprising a Silencer of a Spring Structure of the Present Application The present embodiment differs from embodiment 1 in that the silencer 13 adopts an elastic body of a spring structure. In the present embodiment, four springs arc adopted to form the silencer 13. One end of each spring is installed in an installation hole 12-0 arranged on the positioning plate 12-3 of the radial sealing assembly 12, and the other end of each spring is installed in an installation hole 14-0 of the lower cover 14.

Since the silencer 13 holds up the radial sealing assembly 12, a gap between the upper cover 11 and the upper pressing plate 12-1 of the radial sealing assembly is very small. When the surgical instrument moves in a reciprocating manner, the impact sound produced between the upper pressing plate 12-1 and the upper cover 11 and between the lower pressing plate 12-5 and the lower cover 14 is avoided, thereby realizing a silencing purpose.

Embodiment 4: A Trocar Comprising a Silencer of a Spiral Spring Structure of the Present Application The present embodiment differs from embodiment 3 in that the silencer 13 adopts an elastic body of a spiral spring structure. In the present embodiment, one spiral spring is adopted to form the silencer 13. One end of the spiral spring is installed in an installation hole 12-0 arranged on the positioning plate 12-3 of the radial sealing assembly 12, and the other end of the spring is installed in an installation hole 14-0 of the lower cover 14.

Since the silencer 13 holds up the radial sealing assembly 12, a gap between the upper cover 11 and the upper pressing plate 12-1 of the radial sealing assembly is very small. When the surgical instrument moves in a reciprocating manner, the impact sound produced between the upper pressing plate 12-1 and the upper cover 11 and between the lower pressing plate 12-5 and the lower cover 14 is avoided, thereby realizing a silencing purpose.

It should be noted that the structure disclosed and described herein can he replaced with other structures of a same effect, and the embodiments described in the present application are not an exclusive structure for implementing the present application. Although the preferred embodiments of the present application are already illustrated and described herein, those skilled in the art should clearly know that these embodiments are only examples, and many other changes, improvements and replacements can be made by those skilled in the art without departing from the present application; and therefore, the protection scope of the present application should be defined according to the spirit and scope of the appended claims of the present application.

What is claimed is:

1. A trocar comprising:
   trocar rod; and
   a sheath, wherein an end sealing assembly of the sheath of the trocar further comprises an upper cover, a radial sealing assembly, a silencer and a lower cover;
   wherein the silencer is an elastic body having one end installed on the radial sealing assembly and the other end of the silencer installed on the lower cover; and the radial sealing assembly is installed between the upper cover and the lower cover.

2. The trocar comprising the silencer according to claim 1, wherein that the silencer is an elastic body of a thin-wall tubular structure manufactured from a medical-use elastic material.

3. The trocar comprising the silencer according to claim 2, wherein that the elastic body of the thin.-wall tubular structure of the silencer comprises at least two elastic supporting legs.

4. The trocar comprising the silencer according to claim 1, wherein that the silencer is an elastic body of a spring structure manufactured from a medical-use elastic material.

5. The trocar comprising the silencer according to claim 4, wherein that one end of the silencer of the elastic body of the spring structure is installed in an installation hole of the radial sealing assembly, and the other end is installed in an installation hole of the lower cover.

\* \* \* \* \*